US012114962B2

(12) United States Patent
Olivo et al.

(10) Patent No.: US 12,114,962 B2
(45) Date of Patent: Oct. 15, 2024

(54) PLACEMENT DEVICE FOR MEDICAL OR VETERINARY USE, PLACEMENT TRACKING SYSTEM, AND METHOD FOR TRACKING

(71) Applicant: Agency for Science, Technology and Research, Singapore (SG)

(72) Inventors: Malini Olivo, Singapore (SG); Renzhe Bi, Singapore (SG); Jun Hui Ho, Singapore (SG); Yao Du, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 445 days.

(21) Appl. No.: 17/594,355

(22) PCT Filed: Apr. 15, 2020

(86) PCT No.: PCT/SG2020/050230
§ 371 (c)(1),
(2) Date: Oct. 12, 2021

(87) PCT Pub. No.: WO2020/218971
PCT Pub. Date: Oct. 29, 2020

(65) Prior Publication Data
US 2022/0183563 A1    Jun. 16, 2022

(30) Foreign Application Priority Data
Apr. 23, 2019   (SG) .......................... 10201903629R (51) Int. Cl.
*A61B 5/00*        (2006.01)
*A61B 5/06*        (2006.01)
(Continued)

(52) U.S. Cl.
CPC ............ *A61B 5/0095* (2013.01); *A61B 5/061* (2013.01); *A61B 5/14539* (2013.01); *G01S 5/18* (2013.01); *G01S 11/14* (2013.01); *G01S 11/16* (2013.01)

(58) Field of Classification Search
CPC ... A61B 5/0095; A61B 5/061; A61B 5/14539; G01S 5/18; G01S 11/14; G01S 11/16
See application file for complete search history.

(56) References Cited

U.S. PATENT DOCUMENTS 10,206,607 B2   2/2019  Prough et al.
10,238,299 B2   3/2019  Murakoshi
(Continued)

FOREIGN PATENT DOCUMENTS

WO    2012006607 A2    1/2012

OTHER PUBLICATIONS

Li et al., "Internal-Illumination Photoacoustic Computed Tomography," Journal of Biomedical Optics, vol. 23, No. 3, Mar. 2018, pp. 1-4.
(Continued)

*Primary Examiner* — Joel F Brutus
(74) *Attorney, Agent, or Firm* — Shackelford, McKinley & Norton, LLP (57) ABSTRACT

An aspect relates to a placement device for placement in a medium, including: an elongated optical transmission guide to which a photoacoustic transducer is attached to, wherein the photoacoustic transducer may include a first surface facing away from the second end of the elongated optical transmission guide. The photoacoustic transducer may include a 3-Dimensional shape configured to produce an acoustic signal upon absorption of electromagnetic energy received from the elongated optical transmission guide, and an emission profile of the acoustic signal is based on the
(Continued)

3-Dimensional shape, when the photoacoustic transducer is immersed in homogeneous medium. The placement device may be integral to a medical or veterinary device. An aspect relates to a placement tracking system including the placement device and an ultrasound detector. An aspect relates to a method for tracking a portion of a placement device in a medium using the system.

19 Claims, 6 Drawing Sheets

(51) Int. Cl.
  *A61B 5/145* (2006.01)
  *G01S 5/18* (2006.01)
  *G01S 11/14* (2006.01)
  *G01S 11/16* (2006.01)

(56) References Cited

U.S. PATENT DOCUMENTS

| | | |
|---|---|---|
| 2004/0131299 A1 | 7/2004 | Adoram et al. |
| 2014/0180126 A1 | 6/2014 | Millett et al. |
| 2014/0180135 A1 | 6/2014 | Hoseit et al. |
| 2014/0180316 A1 | 6/2014 | Hoseit |
| 2014/0346329 A1 | 11/2014 | Hirson et al. |
| 2019/0076119 A1* | 3/2019 | Yang .......................... A61B 1/07 |
| 2019/0142277 A1* | 5/2019 | Tokita ..................... A61B 5/444 600/407 |

OTHER PUBLICATIONS

Ai et al., "High Energy Laser Pulse Coupling in a Multimode Fiber for Photoacoustic Tomography," Proc. of SPIE, vol. 9708, pp. 1-6.
Jharia et al., "Utility of Ultrasound/Photoacoustic Imaging for Accurate Catheter Tracking and Temperature Monitoring During Endovenous Laser Ablation," Research Opportunities for Engineering Undergraduates (ROEU) Program at DigitalCommons@WayneState, 2017, pp. 1-2.
International Search Report for International Application No. PCT/SG2020/050230 dated Sep. 21, 2020, pp. 1-4.
Written Opinion of the International Searching Authority for International Application No. PCT/SG2020/050230 dated Sep. 21, 2020, pp. 1-7.
International Preliminary Report on Patentability for International Application No. PCT/SG2020/050230 dated Mar. 22, 2021, pp. 1-16.
Emelianov et al., "Photoacoustics for Molecular Imaging and Therapy," Physics Today, vol. 62, No. 8, May 1, 2009, pp. 34-39.
Xia et al., "Photoacoustic Tomography: Principles and Advances," Progress in Electromagnetics Research, vol. 147, 2014, pp. 1-22.

\* cited by examiner

PLACEMENT DEVICE FOR MEDICAL OR VETERINARY USE, PLACEMENT TRACKING SYSTEM, AND METHOD FOR TRACKING

CROSS-REFERENCE TO RELATED APPLICATION

This application claims the benefit of priority of Singapore Patent Application No. 10201903629R, filed 23 Apr. 2019, the content of which being hereby incorporated by reference in its entirety for all purposes.

TECHNICAL FIELD

An aspect of the disclosure relates to a placement device for placement in a medium. Another aspect of the disclosure relates to a medical or veterinary device configured to be inserted into human or animal tissue. Another aspect of the disclosure relates to a placement tracking system for tracking an object in a medium. Another aspect of the disclosure relates to a method for tracking a portion of a placement device in a medium.

BACKGROUND

The placement of medical devices deep in the body are traditionally confirmed by X-ray imaging which is often time-consuming and costly. It requires highly trained expertise and puts a tremendously amount of pressure on the medical resources allocation. Cheap methods for a specific device such as pH tests for gastric tubes are only good for a binary right or wrong answer. They are not meant for continual monitoring as often required. Thus, there is a need for placement devices which allow for continuous monitoring.

SUMMARY

An aspect of the disclosure relates to a placement device for placement in a medium. The medium may be, for example, human or animal tissue. The placement device may include an elongated optical transmission guide for transmission of electromagnetic energy between a first end and a second end of the elongated optical transmission guide. The placement device may include a photoacoustic transducer attached to the second end of the elongated optical transmission guide. The photoacoustic transducer may include a first surface facing away from the second end of the elongated optical transmission guide. The photoacoustic transducer may include a 3-Dimensional shape configured to produce an acoustic signal upon absorption of electromagnetic energy received from the elongated optical transmission guide. An emission profile of the acoustic signal may be based on the 3-Dimensional shape, when the photoacoustic transducer is immersed in medium, for example in a homogeneous medium. The 3-Dimensional shape may be a pattern of a coating on a core of the photoacoustic transducer. The acoustic signal is preferably ultrasound signal.

An aspect of the disclosure relates to the medical or veterinary device which may be a medical device configured to be inserted into human tissue or to a veterinary device configured to be inserted into animal tissue. The medical or veterinary device may integrally include the placement device as explained herein in accordance with various embodiments. For example, the medical or veterinary device may be selected from: a catheter; an introducer guide wire; a needle; an endoscopy probe; a feeding tube; a combination thereof.

An aspect of the disclosure relates to a placement tracking system for tracking an object in a medium. The placement tracking system may include the placement device or the medical or veterinary device. The placement tracking system may include a light source configured to couple electromagnetic energy into the first end of the elongated optical transmission guide. The placement tracking system may include an ultrasound detector configured to detect the acoustic signal produced by the photoacoustic transducer of the placement device receiving electromagnetic energy via the second end of the elongated optical transmission guide. According to various embodiments, an energy peak of the electromagnetic magnetic energy may overlap with an absorption band of the photoacoustic transducer.

An aspect of the disclosure relates to a method for tracking a portion of a placement device in a medium. The method may include inserting the placement device or inserting the medical or veterinary device into the medium. The method may include positioning an ultrasound detector on or in the medium. The method may include coupling an electromagnetic energy into the first end of the elongated optical transmission guide. The method may include detecting with the ultrasound detector, the acoustic signal produced by the photoacoustic transducer of the placement device receiving electromagnetic energy via the second end of the elongated optical transmission guide.

BRIEF DESCRIPTION OF THE DRAWINGS

The invention will be better understood with reference to the detailed description when considered in conjunction with the non-limiting examples and the accompanying drawings, in which.

DETAILED DESCRIPTION

The following detailed description refers to the accompanying drawings that show, by way of illustration, specific details and embodiments in which the disclosure may be practiced. These embodiments are described in sufficient detail to enable those skilled in the art to practice the disclosure. Other embodiments may be utilized and structural, and logical changes may be made without departing from the scope of the disclosure. The various embodiments are not necessarily mutually exclusive, as some embodiments can be combined with one or more other embodiments to form new embodiments.

Embodiments described in the context of one of the placement devices, medical or veterinary device, placement tracking systems, or methods, are analogously valid for the other of the placement devices, medical or veterinary device, placement tracking systems, or methods. Similarly, embodiments described in the context of a placement devices or a medical or veterinary device are analogously valid for a system or a method, and vice-versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

As used herein, the term "and/or" includes any and all combinations of one or more of the associated listed items.

Present embodiments describe, among others, a placement tracking system for objects in deep tissue using photoacoustic effect. Electromagnetic energy may be delivered exclusively to a photoacoustic transducer integrated with an elongated optical transmission guide, such as an optical fibre. The photoacoustic transducer generates ultrasound waves that may be collected externally by an ultrasound detector. The 3-dimensional placement of the photoacoustic transducer relative to the ultrasound detector can be determined by the acoustic signal. Such configuration enables the location of the photoacoustic transducer deep in the body to be tracked and continually monitored. Thanks to the internal illumination with external source and the transduction efficiency of the photoacoustic transducer, the electromagnetic power requirement is reduced allowing for low power light source to be used. Accessible radiation to the tissue is also minimised as the electromagnetic energy (e.g., laser) preferably does not illuminate the internal tissue. The elongated optical transmission guide and photoacoustic transducer combo can be integrated into various types of medical devices for placement tracking and monitoring including but not limited to catheters, endoscopy probes, feeding tubes, etc.

Figure 1:
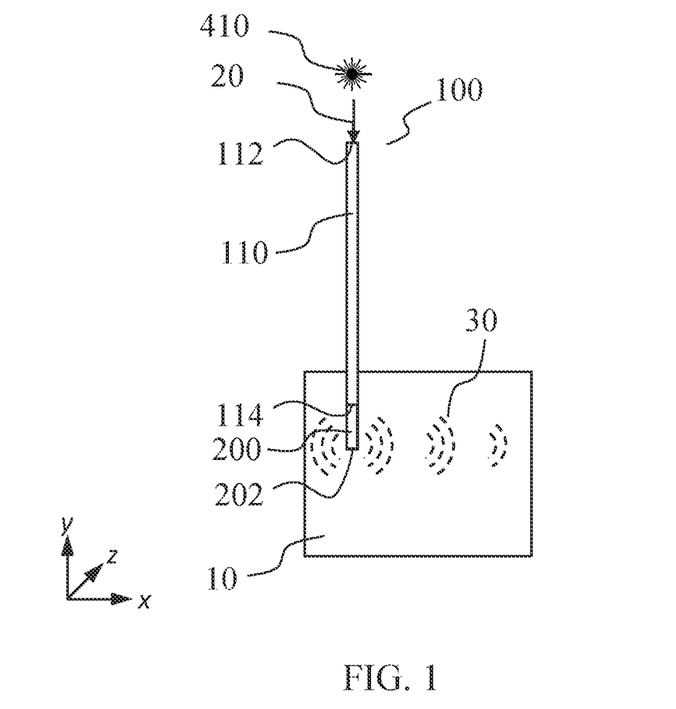
FIG. 1 shows a schematic view of a placement device 100 for placement in a medium 10, in accordance with various embodiments.

FIG. 1 shows a schematic view of a placement device 100 for, and configured to, placement in a medium 10, in accordance with various embodiments.

The placement device 100 may be configured for placement in a medium 10. The expression "placement in" includes the meaning of insertion. In some embodiments, the medium 10 may be biological tissue, for example human or animal tissue. The term "animal" as used herein does not include human. In some embodiments the medium 10 may be in vivo. Alternatively, the medium 10 may be ex vivo. In other embodiments the medium 10 may be a non-biological medium.

Besides integration on a medical device for placement tracking purposes, the placement device 100 may be used with other apparatus including but not limited to photoacoustic imaging system, ultrasound imaging system, etc. as a reference imaging marker in deep tissue. The photoacoustic transducer is an optically driven ultrasound transducer.

The placement device 100 shown in FIG. 1 may include an elongated optical transmission guide 110. The elongated optical transmission guide 110 may be an optical fibre. The elongated optical transmission guide 110 may be flexible. The elongated optical transmission guide 110 may be part of a bundle of optical fibres and/or cables. Alternatively or in addition, the elongated optical transmission guide 110 may itself include a bundle of optical fibers. According to various embodiments, the photoacoustic transducer 200 is non-removable from the elongated optical transmission guide 110.

The elongated optical transmission guide 110 is configured to transmit electromagnetic energy 20 between a first end 112 and a second end 114 of the elongated optical transmission guide 110. For example, the elongated optical transmission guide 110 may be a multi-mode optical fiber configured to guide light, e.g., laser light. The electromagnetic energy 20 may be light, for example laser light, emitted by a light source 410, for example a laser. The electromagnetic energy 20 may be coupled into the elongated optical transmission guide 110, for example into a first end 210. Coupling and/or further transmission optics may be added between the light source and the first end 210.

The placement device 100 shown in FIG. 1 further includes a photoacoustic transducer 200 attached to the second end 114 of the elongated optical transmission guide 110. The photoacoustic transducer 200 may include a first surface 202 facing away from the second end 114 of the elongated optical transmission guide 110. The photoacoustic transducer 200 may be configured to absorb the electromagnetic energy 20 received from the elongated optical transmission guide 110 and, based on the absorbed electromagnetic energy 20, emit acoustic signal 30. For maximum transduction efficiency, the wavelength of the electromagnetic energy 20, e.g., laser, needs to match the absorption peak of the photoacoustic transducer 200. Absorption of electromagnetic energy 20 may be provided by a coating 226. The coating 226 may include a material with a high absorption coefficient matching the wavelength of the electromagnetic energy 20, for which the light source 410 is configured. Further the elongated optical transmission guide 110 is configured to convey electromagnetic energy 20

The photoacoustic transducer 200 may include a 3-Dimensional shape configured to produce an acoustic signal 30 upon absorption of electromagnetic energy 20 received from the elongated optical transmission guide 110. The 3-Dimensional shape may be at least partially defined by the first surface. An emission profile of the acoustic signal 30 may be based on the 3-Dimensional shape, when the photoacoustic transducer 200 is immersed in homogeneous medium. The 3-Dimensional shape may be a pattern of a coating 226 on a core 224 (see FIG. 2) of the photoacoustic transducer. The emission profile of the acoustic signal 30 may be based on the coating 226, when the photoacoustic transducer 200 is immersed in homogeneous medium. Obviously, a medium is required for the transmission of sound, however it is understood that the medium is not part of the placement device 100. A pre-determined emission profile of the acoustic signal 30 may be easiest determined when the medium is homogeneous.

The box in FIG. 1 symbolizes that the medium, in which a measurement may be taken, may be limited to a perimeter (e.g., a human subject), and the remainder of the placement device 100 may be external to this perimeter, for example surrounded by another medium, different from the medium, such as air.

When used in biological tissue, an outer surface of the placement device 100, or at least a portion of the placement device 100 intended for insertion into the biological tissue, is biocompatible with the biological tissue. For example, at least a portion of the placement device 100 including the photoacoustic transducer 200 is biocompatible with human tissue according to ISO 10993-5.

The placement device 100 in accordance with various embodiments may be electrically passive, e.g., free of electric and/or electronic components, and allows for production of photoacoustic signals for deep tissue tracking, without inducing electric or magnetic fields that may interfere with other medical equipment. Further, it allows for tracking without needing a self-powered implant. The skilled person will understand that external components, not intended for insertion in the medium, may have electrical and/or electronic components. Thanks to the efficient delivery and absorption of the bundle included the elongated optical transmission guide 110 and photoacoustic transducer 200, a wide range of wavelengths and absorbing materials can be employed. The wavelength is not limited to near infrared as used in traditional photoacoustic imaging.

Due to the macroscopic size of the photoacoustic transducer as compared to conventional contrast agents (in microscopic powder form), its composition/structure can be tuned for optimal transduction efficiency. For example, the photoacoustic transducer may comprise only one or a plurality of active materials to convert electromagnetic energy to acoustic energy directly. An example of an active material is a contrast agent such as indocyanine green (ICG). Alternatively, the photoacoustic transducer may comprise two or more materials. The surface of the photoacoustic transducer may be a coating that converts electromagnetic energy to heat and the core may be another material with a high Gruneisen constant that converts heat to acoustic signal more efficiently.

Figure 2:
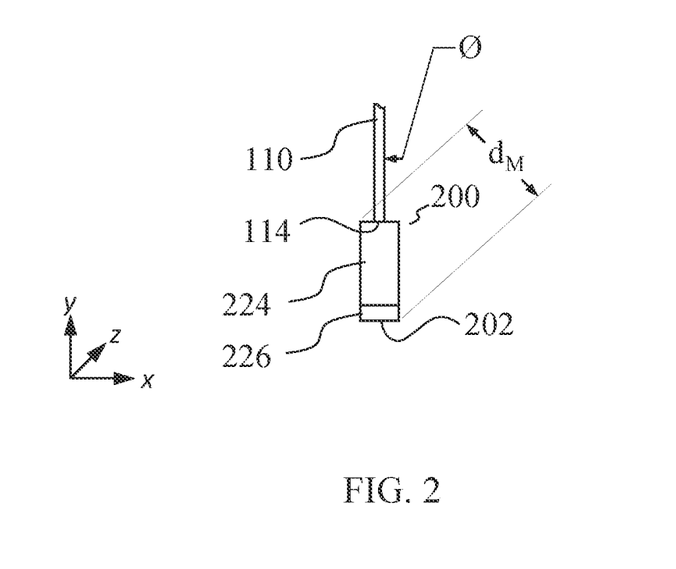
FIG. 2 shows a schematic detailed view of a photoacoustic transducer 200 attached to a second end 114 of an elongated optical transmission guide 110, in accordance with various embodiments.

FIG. 2 shows a schematic detailed view of a photoacoustic transducer 200 attached to a second end 114 of an elongated optical transmission guide 110, in accordance with various embodiments. The photoacoustic transducer 200 may include a first surface 202 facing away from the second end 114 of the elongated optical transmission guide 110. The photoacoustic transducer 200 may include a 3-Dimensional shape configured to produce an acoustic signal 30 upon absorption of electromagnetic energy 20 received from the elongated optical transmission guide 110. An emission profile of the acoustic signal 30 may be based on, e.g. determined by, the 3-Dimensional shape, when the photoacoustic transducer 200 may be immersed in homogeneous medium. The 3-Dimensional shape may be the pattern of the coating 226 on the core 224 of the photoacoustic transducer 200.

According to various embodiments, the photoacoustic transducer 200 may include a core 224 and a coating 226 on the core 224. The core 224 may be fixed to the second end of the optical fiber, for example in the form of a cap. The core 224 provides the structural support to the coating. Thus, core 224 and coating 226 may have an interface with a contact area. The core 224 is at least partially transparent, e.g., transmittance equal or over to 90%, to the electromagnetic energy 20. According to various embodiments, a dimension, such as a greatest dimension ($d_M$), of the photoacoustic transducer 200 may be smaller than 10 times the outer girth of the optical transmission guide 110. The outer girth may be the outer girth of an outer jacket of an optical fibre. In the example of FIG. 2, the outer girth is given by the product $\pi \cdot \emptyset$, wherein $\emptyset$ is the outer diameter of the optical transmission guide 110. For example, the greatest dimension, of the photoacoustic transducer 200 may bet selected from 1.2 mm to 3.5 mm.

According to various embodiments, the first surface 202 may be a surface of the coating 226. In some embodiments, the coating 226 may at least partially surround the core 224. The coating 226 may be configured to convert electromagnetic energy 20 into a heat and the core 224 may be configured to convert the heat into sound for providing the acoustic signal 30. The coating 226 may act as the main absorber that has a high efficiency of absorption of the electromagnetic energy 20 delivered from the elongated optical transmission guide 110. A thickness of the coating 226 may be chosen to allow for sufficient signal generation, depending on the intended application. For example, the thickness of the coating 226 may be chosen between 0.05 micrometer to 500 micrometer.

According to various embodiments, the Gruneisen constant of a material of the core 224 may be greater than a Gruneisen constant of a material of the coating 226.

According to various embodiments the coating 226 may include an absorption coefficient greater than an absorption coefficient of the core 224 for a same pre-determined wavelength of the electromagnetic energy 20.

According to various embodiments, the emission profile of the photoacoustic transducer 200 in homogeneous medium may be based on the 3-Dimensional shape of the photoacoustic transducer 200. For example, the 3-Dimensional shape of the pattern of the coating 226 on the core 224 may define the emission profile of the photoacoustic transducer 200 in homogeneous medium.

Figure 3:
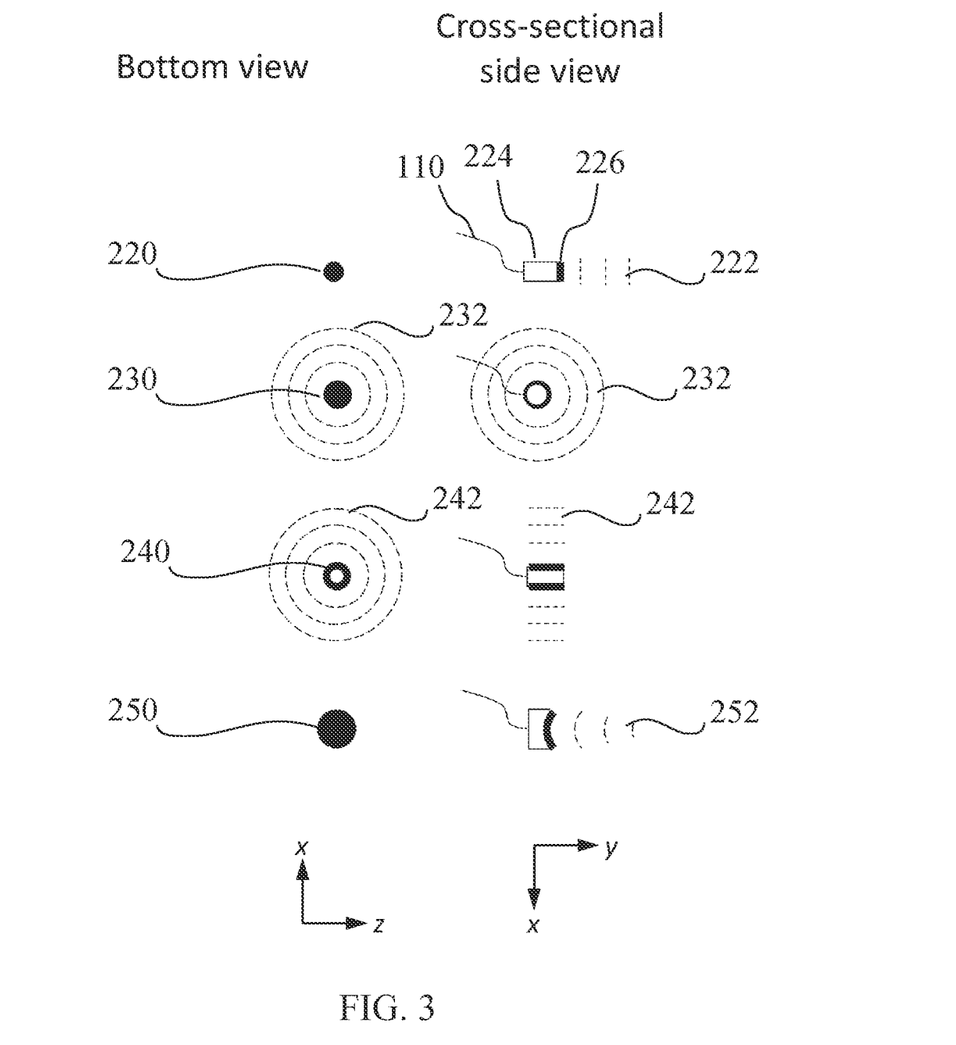
FIG. 3 shows schematic views of photoacoustic transducers 200 including different 3-Dimensional shapes, in accordance with various embodiments.

FIG. 3 shows schematic views of photoacoustic transducers 200 including different 3-Dimensional shapes provided by different patterns of coating 226, in accordance with various embodiments. The exemplary photoacoustic transducers 200 are shown on the left side of the figure in bottom view in plane x-z, and on the right side in a cross-sectional side view in plane x-y. Non-limiting 3-Dimensional shape examples are a disk 220, a convex spherical cap 230, a tube 240, a cylinder, a concavity such as a concave spherical cap 250. According to various embodiments, if not otherwise explicitly stated, concave or convex refers to the first surface 202 facing away from the second end 114 of the elongated optical transmission guide 110.

According to some embodiments, the 3-Dimensional shape may be a disk 220 having a cylindrical shape wherein a height may be smaller than a diameter. For example, one or each of both bases of the cylindrical shape may be flat and parallel to each other. A height may be a thickness of the coating 226, further, the thickness may be substantially uniform. The first surface 202 may be a base of the cylindrical shape which is flat. According to various embodiments, the disk 220 may be a solid disk 220. In the non-limiting example of FIG. 3, the 3-Dimensional shape 220 is a disk 220 shown in bottom view (left side of FIG. 3). It can be seen from the cross-sectional side view (right side of FIG. 3) that the emission profile 222 of the acoustic signal 30 is mainly parallel and in the direction away from the second surface.

According to some embodiments, the 3-Dimensional shape may be substantially spherical, e.g. it may be a spherical cap 230. For example, the spherical cap 230 may be a half-sphere, or may be substantially spherical, or fully spherical except for the coupling and/or connection with the elongated optical transmission guide 110. The spherical cap may be achieved with a spherical cap shaped core, or a spherical core, having its surface substantially coated with coating 226, for example 50% or more, 75% or more, 90% or more, or between 90% and 98%, of the core's 224 surface. The thickness of the coating 226 may be substantially uniform. In the non-limiting example of FIG. 3, the 3-Dimensional shape 230 is a sphere 230 shown in the bottom view (left side of FIG. 3). In the cross-sectional side view (right side of FIG. 3) the emission profile in plane x-y can be seen. The emission profile 232 of the acoustic signal 30 is spherical and in the direction away from the second surface, thus, divergent in all directions.

According to some embodiments, the 3-Dimensional shape may be a cylinder having a cylindrical shape wherein a height may be equal to or larger than a diameter. For example, one or each of both bases of the cylinder may be flat and parallel to each other. In other embodiments the first surface may be a base of the cylinder which is concave or convex. According to some embodiments, the cylinder may be a solid cylinder, optionally regular. Alternatively, the cylinder may be a hollow cylinder, optionally regular. In the non-limiting example of FIG. 3, the 3-Dimensional shape 240 is a hollow regular cylinder 240 shown in the bottom view (left side of FIG. 3) in which the annular surface formed by the thickness of the coating 226 can be seen. In the cross-sectional side view (right side of FIG. 3), the emission profile in plane x-y can be seen. The emission profile 242 of the acoustic signal 30 is cylindrical, thus, divergent.

According to some embodiments, the first surface 202 may be concave. A concave first surface 202 may generate an emission profile which is convergent as the distance to the first surface 202 increases, at least until a point of maximum convergence. For example, the concave surface may be configured to focus the acoustic signal 30 on a focal point. In the non-limiting example of FIG. 3, the 3-Dimensional shape 250 is a disk 220 shown in bottom view (left side of FIG. 3). It can be seen from the cross-sectional side view (right side of FIG. 3) that the emission profile 252 of the acoustic signal 30 is focused in the direction away from the second surface.

According to various embodiments, the size of the photoacoustic transducer 200 dictates the frequency of the ultrasound and its strength. These two parameters have an effect on the penetration depth as human tissue scatters ultrasound to different extents based on its frequency. However, depending on the application, there will be limits on the size of the placement device 100, e.g. of an optical fibre-photoacoustic transducer 200 bundle. For example, to be integrated to intravascular catheters, the placement device 100 needs to be smaller than the diameter of an artery. Therefore, the optimal size is determined by the balance between signal quality and feasibility. For deep tissue tracking of medical tubes such as endotracheal and nasogastric tubes, photoacoustic transducer 200 as large as 5 mm may be used. For underneath skin tracking of catheters, photoacoustic transducer 200 as small as 1 mm may provide signals strong enough for detection.

According to some embodiments, the first surface 202 may be convex. A convex first surface 202 may generate an emission profile which is divergent as the distance to the first surface 202 increases.

According to various embodiments, the core is a 3-Dimensional solid, wherein one of 3 orthogonal dimensions is preferably within 10× greater or smaller than the other dimension. In an example, the 3-Dimensional solid may be a cylinder, the 3 orthogonal dimensions being height, and first and second orthogonal diameters of the largest base or of any of the two bases in the case of a regular cylinder. Examples of core including regular cylinder having a height greater than a diameter of a base are shown in FIG. 3, see core 224 used in conjunction with 3-Dimensional shapes 220, 230, and 240. In another example, the 3-Dimensional solid may be a rectangle, a prism, e.g., a regular prism having a n-sided polygonal base. Examples of polygonal base may be polygons with n selected from the range of 3 to 20, for example regular polygons, wherein n may optionally be selected from the range of 3 to 20. The 3 orthogonal dimensions are height, and first and second orthogonal diameters of the largest base or of any of the two bases in the case of a regular prism. According to various embodiments, the core is solid, thus not hollow. The skilled person in the art would understand that the core may include cavities, e.g., for forming convex surfaces, while still being a solid. Using a 3-Dimensional solid together with the coating enables fabrication of photoacoustic transducer having different emission profiles of acoustic signals.

According to various embodiments the electromagnetic energy 20 may be laser light, and wherein the laser light may be applied as a modulated signal, optionally as a pulsed signal.

According to various embodiments the elongated optical transmission guide 110 may be an optical fibre.

According to various embodiments, the optical fibre may be a multimode optical fibre.

Figure 4:
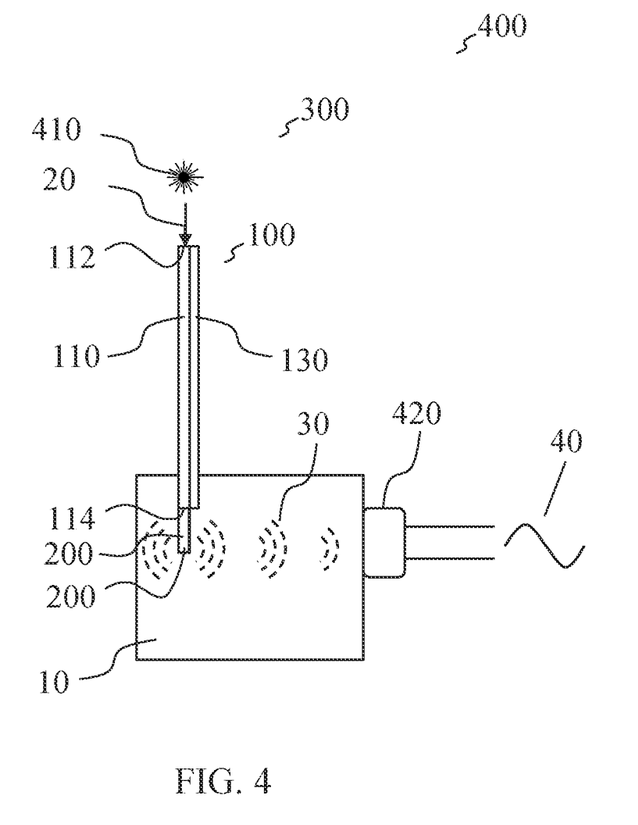
FIG. 4 shows a schematic view of a placement tracking system 400 including a placement device 100, a light source 410, and an ultrasound detector 420, in accordance with various embodiments.

FIG. 4 shows a schematic view of a placement tracking system 400 including a placement device 100, a light source 410, and an ultrasound detector 420, in accordance with various embodiments. The placement device 100 may be according to embodiments described herein. The light source 410 may be configured to couple electromagnetic energy 20 into the first end 112 of the elongated optical transmission guide 110. The elongated optical transmission guide 110 is configured to convey the electromagnetic energy 20 from the first end 112 to the second end 114. The photoacoustic transducer 200 receives the electromagnetic energy 20 via the second end 114, and generates the acoustic signal 30. When photoacoustic transducer 200 contacts, e.g., is inserted into, a medium, the medium 10 transmits the acoustic signal 30. The placement device 100 may further include an ultrasound detector 420 configured to detect the acoustic signal 30 produced by the photoacoustic transducer 200 and transmitted by the medium 10. The system in accordance to various embodiments allows 3-dimensional device placement tracking in deep tissue which is not possible by traditional X-ray imaging.

According to various embodiments, the ultrasound detector 420 may convert sound waves into an electrical signal 40, for example into a voltage signal or a current signal. An electric signal may be converted into a digital signal for digital signal processing. According to various embodiments, the ultrasound detector may include one single ultrasound transducer or a plurality of ultrasound transducers, which are configured to receive ultrasound and generate electric signal, in other words also named as ultrasound to electric transducer. For example, the ultrasound detector may be a non-imaging detector or an imaging detector. The detector may be an array of transducers for simultaneous detection at various locations and angle for faster placement determination.

According to various embodiments an energy peak of the electromagnetic magnetic energy overlaps with an absorption band of the photoacoustic transducer 200.

An aspect of the disclosure also concerns medical or veterinary device 300 configured to be inserted into human or animal tissue. The device 300 may be a medical device configured to be inserted into human tissue. Alternatively or in addition, the device 300 may be a veterinary device 300 configured to be inserted into tissue. The medical and/or veterinary device 300 may include the placement device 100 as explained in accordance with various embodiments. For example, the placement device 100 may be removable or non-removable coupled to a medical instrument 130 such as a catheter; an introducer guide wire; a needle; an endoscopy probe; a feeding tube; a combination thereof. The medical and/or veterinary device 300 may include the placement device 100 and the medical instrument 130, and the medical and/or veterinary device 300 may itself be a catheter; an introducer guide wire; a needle; an endoscopy probe; a feeding tube; a combination thereof.

Figure 5:
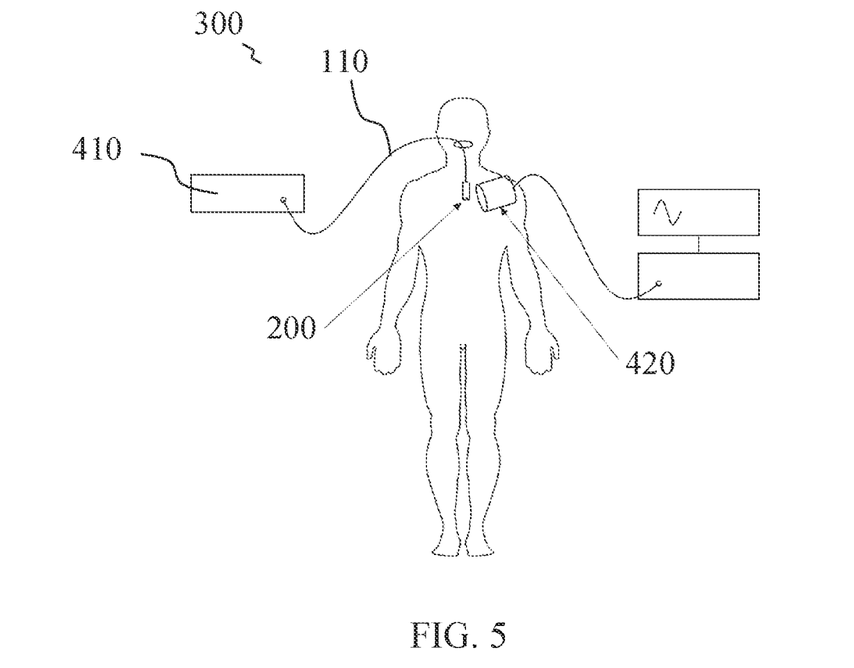
FIG. 5 shows an exemplary application of the medical or veterinary device 300 in accordance with various embodiments.

FIG. 5 shows an exemplary application of the medical or veterinary device 300 in accordance with various embodiments. FIG. 5 shows a schematic view of a human body, in which the placement device 100, for example as part of an endoscope 300, is inserted orally into the body. Electromagnetic energy, such as laser, is provided by the light source 410, for example, in the form of pulses and coupled into elongated optical transmission guide 110, for example an optical fibre. The photoacoustic transducer 200 produces an acoustic signal 30 upon absorption of electromagnetic energy 20 received from the elongated optical transmission guide 110. The generated acoustic energy propagates through the body. A single ultrasound transducer outside of the body is sufficient for detecting this energy (from the acoustic signal 30) and translate it to an intensity readout. Thus, the position of the photoacoustic transducer 200, which corresponds to the end of the endoscope 300, may be easily tracked externally by an ultrasound detector 420. The system in accordance with various embodiments is a photoacoustic beaconing and detection system which provides precise 3-dimensional information on the placement of medical devices in deep tissue. The electrical signal obtained from the ultrasound detector 420 may be amplified and analyzed as desired. Examples of such electrical signals will be shown below in connection with an experimental setup shown in FIG. 6.

Figure 6:
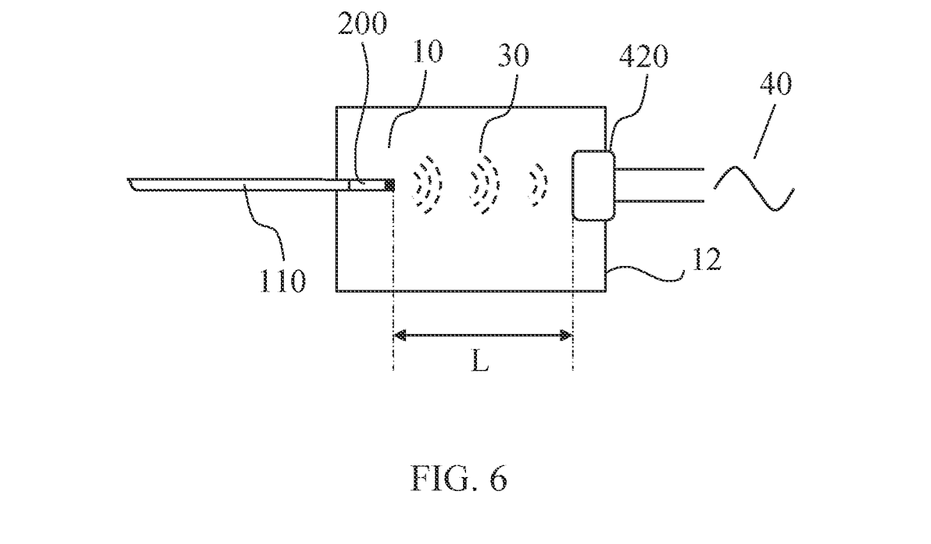
FIG. 6 shows an experimental setup used for measurements.

In FIG. 6, a schematic experimental setup is shown in top view, a tank 12 is filled with water as medium 10. An elongated optical transmission guide 110 is positioned such that the photoacoustic transducer 200 is submerged into the water. An ultrasound detector 420 is positioned such that its sensing surface is submerged in the water. For measuring an intensity of the acoustic signal 30 over distance L, the photoacoustic transducer 200 and the ultrasound detector 420 are placed facing each other at a separation distance L.

In a comparative photoacoustic imaging system, where medium (e.g. tissue) is directly impinged with laser, the highest penetration depth is in the vicinity of 5 cm as achieved in photoacoustic computed tomography (PAT). The penetration depth is limited by the scattering of near infrared electromagnetic waves in the tissue, therefore the optical energy cannot reach any deep tissue. In contrast, in the placement device 100 in accordance with various embodiments, no scattering in the medium takes place. Thanks to the high transduction efficiency, lower laser power is required to generate significant acoustic signal. The detection depth is no longer limited by the optical propagation but the acoustic propagation which can be much farther.

In an example, an ex vivo experiment was conducted using the experimental setup as shown in FIG. 6. In this experimental setup, the photoacoustic transducer 200 used was a fiber dust cap as core and carbon paint as coating. The carbon paint was supported by an aluminum diaphragm however the invention is not limited thereto, and the coating (e.g. carbon paint) may be supported by the core. According to various embodiments, the coating may be applied directly on the core, e.g. via adhesive, coating, or other method of deposition. The medium between the photoacoustic transducer 200 and the ultrasound detector 420 was water. The sound wave (acoustic signal) detected by the ultrasound detector 420 was displayed on an oscilloscope as a voltage in mV. The pulse energy of the laser, having peak wavelength at 532 nm, was 8.6 µJ and the pulse frequency was 5 kHz. The pulse energy is 4 orders of magnitude lower than the 30 mJ typically used in PAT.

Figure 7:
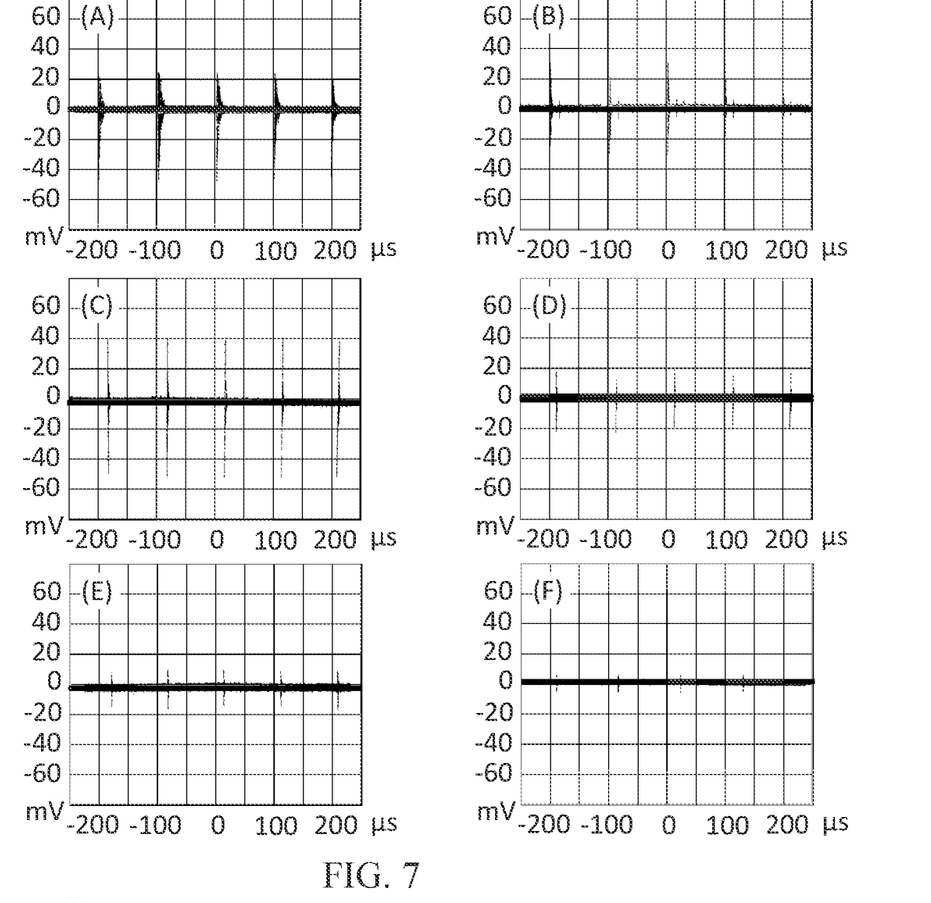
FIG. 7 shows photoacoustic signals detected at various distances, with the experimental setup as shown in FIG. 6; the oscillograms are photographed and may therefore be distorted, however the data can be read with assistance of the oscillograms' tic marks and grids.

FIG. 7 shows photoacoustic signals detected at various distances, with the experimental setup as shown in FIG. 6; the oscillograms are photographed and may therefore be distorted, however the data can be read with assistance of the oscillograms' tic marks and grids. FIG. 7 shows the oscillograms obtained when the photoacoustic transducer and the ultrasound detector are placed at various separation distances (L) from 0 cm to 20 cm, namely L=(A) 0 cm, (B) 2 cm, (C) 5 cm, (D) 10 cm, (E) 15 cm, and (F) 20 cm. Note the distance in the echo among (A) and (B). A horizontal shift was applied in (C), (D), (E) and (F) for visual clarity.

Figure 8:
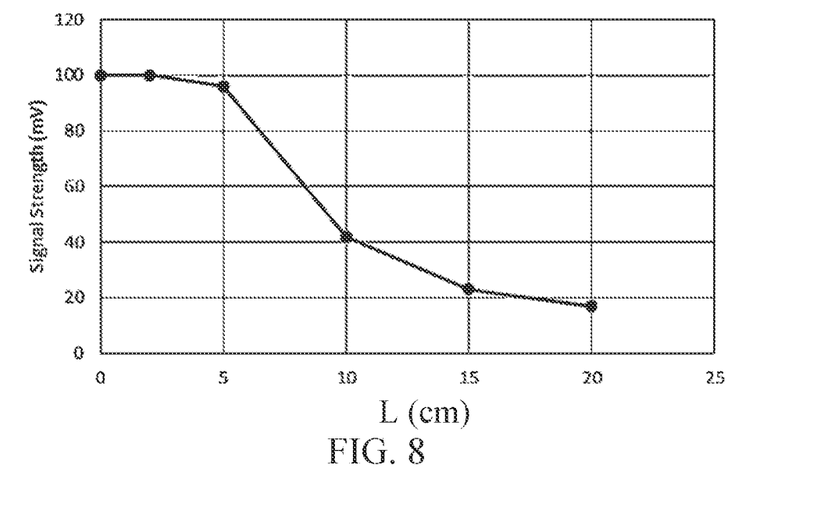
FIG. 8 is a plot of the relative acoustic signal strength as measured in mV by the ultrasound detector 420 and against the separation distance in cm between the photoacoustic transducer 200 and the ultrasound detector 420.

FIG. 8 shows a plot of the relative acoustic signal strength as measured in mV by the ultrasound detector 420 and against the separation distance in cm between the photoacoustic transducer 200 and the ultrasound detector 420. Clear acoustic signal is detected at all separation distances and the signal intensity correlates with the separation distance. No signal is detected off-axis of the propagation pathway. This allows for 3-dimensional placement tracking which is not possible by traditional method such as X-ray imaging.

Figure 9:
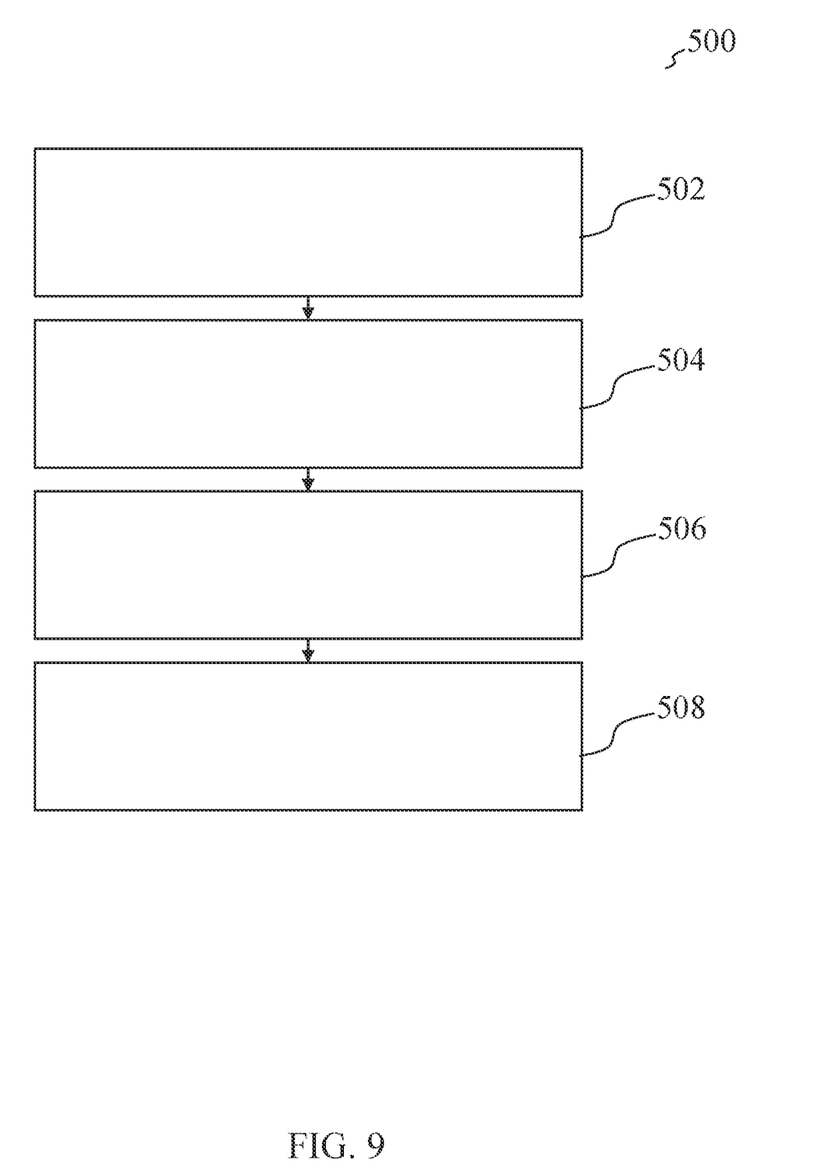
FIG. 9 is a schematic flowchart of a method 500 in accordance with various embodiments, or tracking a portion of a placement device 100 in a medium 10.

FIG. 9 is a schematic flowchart of a method 500 in accordance with various embodiments, or tracking a portion of a placement device 100 in a medium 10. The method may include inserting 502 the placement device 100 or the medical or veterinary device 300 including the placement device 100, into the medium 10. The method may further include positioning 504 an ultrasound detector 420 on the medium 10. The method may further include coupling 506 an electromagnetic energy 20 into the first end 112 of the elongated optical transmission guide 110. The method may further include detecting 508 with the ultrasound detector 420, the acoustic signal 30 produced by the photoacoustic transducer 200 of the placement device 100 receiving electromagnetic energy 20 via the second end 114 of the elongated optical transmission guide 110.

According to various embodiments, the method 500 may further include repeating the positioning 504, the coupling 506, and the detecting 508 for a plurality of different locations of the ultrasound detector 420 on or in the medium 10 to obtain a plurality of acoustic signals 30; and selecting a strongest acoustic signal of the plurality of acoustic signals 30 as a nearest detected lateral location of the photoacoustic transducer 200 of the placement device 100.

According to various embodiments, the method 500 may further include determining a distance between the photoacoustic transducer 200 of the placement device 100 and the ultrasound detector 420. The distance may be determined based on an absolute intensity of the acoustic signal 30 detected by the ultrasound detector 420. Alternatively or in addition, the distance may be determined based on a propagation delay between the coupling 506 of the electromagnetic energy 20 into the first end 112 of the elongated optical transmission guide 110 and a detection 508 by the ultrasound detector 420, the acoustic signal 30. For example, the absolute intensity may be compared to a calibrated table including absolute intensities and their respective distances for a medium. For example, the propagation delay may be compared to a calibrated table including propagation delays and their respective distances for a medium. In some embodiments, any of the tables may be generated by using identical placement systems, and configured with the same electromagnetic energy settings, such as power and wavelength, when using the system and when generating any of the tables, alternatively, correction coefficients may be employed. The lateral location of the photoacoustic transducer may be determined from the location where the signal is the strongest and the depth may be determined from the absolute intensity and/or the propagation delay.

According to various embodiments, in practice, lateral location may be determined by the appearance of the signal and the depth may be determined from the attenuation.

A photoacoustic transducer at the tip of the optical fibre, in accordance with various embodiments, absorbs the electromagnetic energy to generate acoustic signal. In contrast, all other photoacoustic imaging/sensing methods directs light either externally or internally to the tissue for it to absorb the electromagnetic energy. The carefully designed photoacoustic transducer of the present application maximises the light-acoustic energy conversion efficiency and optimises the acoustic propagation pathway. This allows for lower energy laser source to be used for high resolution localisation. The system achieves 3-D localisation, even using a single ultrasound probe, with the controlled and tuneable photoacoustic transducer.

While the disclosure has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A placement device for placement in a medium, comprising:
an elongated optical transmission guide for transmission of electromagnetic energy between a first end and a second end of the elongated optical transmission guide;
a photoacoustic transducer attached to the second end of the elongated optical transmission guide,
wherein the photoacoustic transducer comprises a first surface facing away from the second end of the elongated optical transmission guide,
wherein the photoacoustic transducer comprises a 3-Dimensional shape configured to produce an acoustic signal upon absorption of electromagnetic energy received from the elongated optical transmission guide;
wherein the photoacoustic transducer comprises a core and a coating on the core, and wherein the first surface is a surface of the coating, and
wherein the coating contacts or at least partially surrounds the core and is configured to convert electromagnetic energy into a heat and wherein the core is configured to convert the heat into sound for providing the acoustic signal, wherein the Grüneisen constant of a material of the core is greater than a Grüneisen constant of a material of the coating.

2. The placement device of claim 1, wherein the 3-Dimensional shape is a disk having a cylindrical shape wherein a height is smaller than a diameter.

3. The placement device of claim 1, wherein the first surface is convex.

4. The placement device of claim 1, wherein the first surface is concave.

5. The placement device of claim 1, wherein the 3-Dimensional shape is a cylinder having a cylindrical shape wherein a height is equal to or larger than a diameter.

6. The placement device of claim 1, wherein the 3-Dimensional shape is a pattern of the coating on the core.

7. The placement device of claim 1, wherein the coating comprises an absorption coefficient greater than an absorption coefficient of the core for a same pre-determined wavelength of the electromagnetic energy.

8. The placement device of claim 1, wherein the electromagnetic energy is laser light, and wherein the laser light is applied as a modulated signal, optionally as a pulsed signal.

9. The placement device of claim 1, wherein the elongated optical transmission guide is an optical fibre.

10. The placement device of claim 1, wherein the photoacoustic transducer is non-removable from the elongated optical transmission guide.

11. The placement device of claim 1, wherein the medium is biological tissue, the placement device is configured to be placed into biological tissue, and an outer layer of at least a portion of the placement device (comprising the photoacoustic transducer is biocompatible with the biological tissue.

12. The placement device of claim 11, wherein the biological tissue is human or animal tissue.

13. A medical or veterinary device configured to be inserted into human or animal tissue, respectively, wherein the medical or veterinary device integrally comprises a placement device comprising:
an elongated optical transmission guide for transmission of electromagnetic energy between a first end and a second end of the elongated optical transmission guide;
a photoacoustic transducer attached to the second end of the elongated optical transmission guide,
wherein the photoacoustic transducer comprises a first surface facing away from the second end of the elongated optical transmission guide,
wherein the photoacoustic transducer comprises a 3-Dimensional shape configured to produce an acoustic signal upon absorption of electromagnetic energy received from the elongated optical transmission guide;
wherein the photoacoustic transducer comprises a core and a coating on the core, wherein the first surface is a surface of the coating,
wherein the coating contacts or at least partially surrounds the core and is configured to convert electromagnetic energy into a heat and wherein the core is configured to convert the heat into sound for providing the acoustic signal, wherein the Grüneisen constant of a material of the core is greater than a Grüneisen constant of a material of the coating; and wherein an outer layer of at least a portion of the placement device comprising the photoacoustic transducer is biocompatible with the human or animal tissue.

14. The medical or veterinary device of claim 13 being selected from:
a catheter;
an introducer guide wire;
a needle;
an endoscopy probe;
a feeding tube;
a combination thereof.

15. A placement tracking system for tracking an object in a medium, the placement tracking system comprising:
a placement device comprising:
an elongated optical transmission guide for transmission of electromagnetic energy between a first end and a second end of the elongated optical transmission guide;
a photoacoustic transducer attached to the second end of the elongated optical transmission guide,
wherein the photoacoustic transducer comprises a first surface facing away from the second end of the elongated optical transmission guide,
wherein the photoacoustic transducer comprises a 3-Dimensional shape configured to produce an acoustic signal upon absorption of electromagnetic energy received from the elongated optical transmission guide;
wherein the photoacoustic transducer comprises a core and a coating on the core, and wherein the first surface is a surface of the coating, and
wherein the coating contacts or at least partially surrounds the core and is configured to convert electromagnetic energy into a heat and wherein the core is configured to convert the heat into sound for providing the acoustic signal,
wherein the Grüneisen constant of a material of the core is greater than a Grüneisen constant of a material of the coating;
a light source configured to couple electromagnetic energy into the first end of the elongated optical transmission guide; and
an ultrasound detector configured to detect the acoustic signal produced by the photoacoustic transducer of the placement device receiving electromagnetic energy via the second end of the elongated optical transmission guide.

16. The placement tracking system of claim 15, wherein an energy peak of the electromagnetic magnetic energy overlaps with an absorption band of the photoacoustic transducer.

17. A method for tracking a portion of a placement device in a medium, the method comprising:
inserting a placement device into the medium, the placement device comprising:
an elongated optical transmission guide for transmission of electromagnetic energy between a first end and a second end of the elongated optical transmission guide;
a photoacoustic transducer attached to the second end of the elongated optical transmission guide,
wherein the photoacoustic transducer comprises a first surface facing away from the second end of the elongated optical transmission guide,
wherein the photoacoustic transducer comprises a 3-Dimensional shape configured to produce an acoustic signal upon absorption of electromagnetic energy received from the elongated optical transmission guide;
wherein the photoacoustic transducer comprises a core and a coating on the core, and wherein the first surface is a surface of the coating, and
wherein the coating contacts or at least partially surrounds the core and is configured to convert electromagnetic energy into a heat and wherein the core is configured to convert the heat into sound for providing the acoustic signal,
wherein the Grüneisen constant of a material of the core is greater than a Grüneisen constant of a material of the coating;
positioning an ultrasound detector on or in the medium;
coupling an electromagnetic energy into the first end of the elongated optical transmission guide;
detecting by the ultrasound detector, the acoustic signal produced by the photoacoustic transducer of the placement device receiving electromagnetic energy via the second end of the elongated optical transmission guide.

18. The method of claim 17, further comprising:
repeating the positioning, the coupling, and the detecting for a plurality of different locations of the ultrasound detector on or in the medium to obtain a plurality of acoustic signals; and
selecting a strongest acoustic signal of the plurality of acoustic signals as a nearest detected lateral location of the photoacoustic transducer of the placement device.

19. The method of claim 17, further comprising:
determining a distance between the photoacoustic transducer of the placement device and the ultrasound detector based on:
an absolute intensity of the acoustic signal detected by the ultrasound detector;
a propagation delay between the coupling of the electromagnetic energy into the first end of the elongated optical transmission guide and a detection by the ultrasound detector, the acoustic signal; or
a combination thereof.

* * * * *